(12) United States Patent
Adams et al.

(10) Patent No.: US 9,241,780 B2
(45) Date of Patent: Jan. 26, 2016

(54) TRANS-VAGINAL SLING DELIVERY DEVICE

(71) Applicant: Empire Technology Development LLC, Wilmington, DE (US)

(72) Inventors: John Mathew Adams, Snohomish, WA (US); Daniel Hawkins, Bellevue, WA (US)

(73) Assignee: Empire Technology Development LLC, Wilmington, DE (US)

( * ) Notice: Subject to any disclaimer, the term of this patent is extended or adjusted under 35 U.S.C. 154(b) by 121 days.

(21) Appl. No.: 14/112,036

(22) PCT Filed: Dec. 18, 2012

(86) PCT No.: PCT/US2012/070340
§ 371 (c)(1),
(2) Date: Oct. 16, 2013

(87) PCT Pub. No.: WO2014/098805
PCT Pub. Date: Jun. 26, 2014

(65) Prior Publication Data
US 2014/0171730 A1    Jun. 19, 2014

(51) Int. Cl.
*A61F 2/00* (2006.01)
(52) U.S. Cl.
CPC .................................. *A61F 2/0045* (2013.01)
(58) Field of Classification Search
CPC ... A61F 2/0004; A61F 2/0031; A61F 2/0036; A61F 2/0045

USPC ........................................................ 600/29–32
See application file for complete search history.

(56) References Cited

U.S. PATENT DOCUMENTS

| 5,464,403 | A | 11/1995 | Kieturakis et al. |
| 2010/0256442 | A1 | 10/2010 | Ogdahl et al. |
| 2011/0237878 | A1 | 9/2011 | Browning |

FOREIGN PATENT DOCUMENTS

| WO | 02078548 A1 | 10/2002 |
| WO | 2012083159 A | 6/2012 |

OTHER PUBLICATIONS

International Search Report and Written Opinion for PCT/US12/70340 filed Dec. 18, 2012, mailed Apr. 15, 2013.

*Primary Examiner* — John Lacyk
(74) *Attorney, Agent, or Firm* — Turk IP Law, LLC

(57) ABSTRACT

Technologies are generally provided for a trans-vaginal sling delivery device for deploying a sub-urethral sling to treat urinary incontinence. A delivery tool coupled with an interior of a delivery tube may be advanced through the vagina, and a pointed end of the delivery tube may puncture the vaginal wall. A sub-urethral sling may be attached to the delivery tube, and the sling may be longitudinally wrapped into a reduced delivery profile around the delivery tool within the delivery tube. The delivery tube may include a longitudinal slit opening, and the sling may be deployed from the delivery tool by rotating the delivery tool. Two delivery tubes and delivery tools may be employed to deploy each end of the sling, such that each end of the sling may be anchored on a right and left side of the urethra with a portion of the sling supporting the urethra from beneath.

23 Claims, 7 Drawing Sheets

TRANS-VAGINAL SLING DELIVERY DEVICE

This Application is the National Stage filing under 35 U.S.C. §371 of PCT Application Ser. No. PCT/US12/70340 filed on Dec. 18, 2012. The disclosure of the PCT Application is hereby incorporated by reference in its entirety.

BACKGROUND

Unless otherwise indicated herein, the materials described in this section are not prior art to the claims in this application and are not admitted to be prior art by inclusion in this section.

Female urinary stress incontinence is a common ailment affecting more than 2 million women annually. Urinary control relies on the finely coordinated activities of the smooth muscle tissue of the urethra and bladder, skeletal muscle, voluntary inhibition, and the autonomic nervous system. Urinary stress incontinence can result from anatomic, physiologic, or pathologic (disease) factors due to aging and childbirth, and can eventually cause inadequate urinary storage or control which may result in bladder leakage. Some effective treatments for incontinence the surgical implantation of device called slings that provide mechanical support for the urethra when pelvic organs shift during points of stress including coughing, sneezing, and laughing, for example. Sling implantation generally involves small skin incisions as well as an incision through the upper vaginal wall to gain appropriate access to position the sling beneath the urethra. Some current sling insertion techniques involve using bulky delivery tools and/or sling containment devices, which can generate significant tissue separation and therefore bleeding to enable implantation. Additionally, the force required on the delivery tool to position the bulky sling devices may cause significant patient discomfort and may require anesthesia.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some example embodiments, the present disclosure describes a trans-vaginal delivery device for positioning a sub-urethral sling. The trans-vaginal delivery device may include a delivery tube having a substantially pointed distal end for puncturing a wall of a vagina and having a longitudinal slit opening along the delivery tube, a sub-urethral sling configured to be wrapped into a reduced delivery profile for delivery through the delivery tube, and a delivery tool coupled with an interior portion of delivery tube, the delivery tool configured to deploy the sub-urethral sling in a position for supporting the urethra.

According to some examples, the present disclosure describes a trans-vaginal delivery device for positioning a sub-urethral sling. The trans-vaginal delivery device may include a first delivery tube having a substantially pointed distal end and having a longitudinal slit opening along the first delivery tub, the first delivery tube configured to advance through the vagina and puncture through an upper wall of the vagina, a first delivery tool coupled with the first delivery tube, the first delivery tool configured to deploy a first end of the sub-urethral sling out of the first delivery tube through the longitudinal slit opening, a second delivery tube having a substantially pointed distal end and having a longitudinal slit opening along the second delivery tube, and a second delivery tool coupled with an interior of the second delivery tube, the second delivery tube and the second delivery tool configured to pass through the puncture in the upper wall of the vagina, wherein the second delivery tool may be configured to deploy a second end of the sub-urethral sling out of the second delivery tube through the longitudinal slit opening.

According to other examples, the present disclosure describes a method for delivering a sub-urethral sling employing a trans-vaginal delivery device. The method may include advancing a delivery tube having a longitudinal slit opening along the delivery tube and having a substantially pointed distal end through a vagina such that an upper interior wall of the vagina may be punctured, coupling a delivery tool with an interior portion of the delivery tube, attaching a first end of a sub-urethral sling to the delivery tube, wrapping a sub-urethral sling in a reduced delivery profile around the delivery tool, passing the delivery tube including the delivery tool and attached sub-urethral sling through the punctured upper interior wall of the vagina, and deploying the sub-urethral sling in a position for supporting the urethra.

According to other examples, the present disclosure describes a method for delivering a sub-urethral sling employing a trans-vaginal delivery device. The method may include employing a first delivery tube having a substantially pointed distal end and having a longitudinal opening along the first delivery tube for enabling a first delivery tool to deploy and position a first end of the sub-urethral sling in a position above and on one of the right side and the left side of the urethra, and employing a second delivery tube having a longitudinal opening along the second delivery tube for enabling a second delivery tool to deploy and position a second end of the sub-urethral sling in a position above and on the other of the right side and the left side of the urethra.

According to other examples, the present disclosure describes a system for delivering a sub-urethral sling employing a trans-vaginal delivery device. The system may include a delivery tube having a substantially pointed distal end for puncturing a wall of a vagina and having a longitudinal slit opening along the delivery tube, a sub-urethral sling configured to be wrapped into a reduced delivery profile for delivery through the delivery tube, and a delivery tool coupled with an interior portion of delivery tube, the delivery tool configured to deploy the sub-urethral sling in a position for supporting the urethra.

According to further examples, the present disclosure also describes a method of manufacturing a trans-vaginal delivery device for delivery of a sub-urethral sling. The method may include forming a delivery tube having a substantially pointed distal end for puncturing a wall of a vagina and having an opening longitudinally along the delivery tube, configuring a sub-urethral sling to be wrapped into a reduced delivery profile for delivery through the delivery tube, and coupling a delivery tool with an interior portion of the delivery tube, the delivery tool configured to advance the sub-urethral sling through the delivery tube to deploy the sub-urethral sling in a position for supporting the urethra. The method may include configuring the delivery tube to have a substantially circular cross sectional shape with a diameter in a range configured to enable the delivery tool and the sub-urethral sling in the reduced delivery profile to fit within a hollow interior of the delivery tube.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
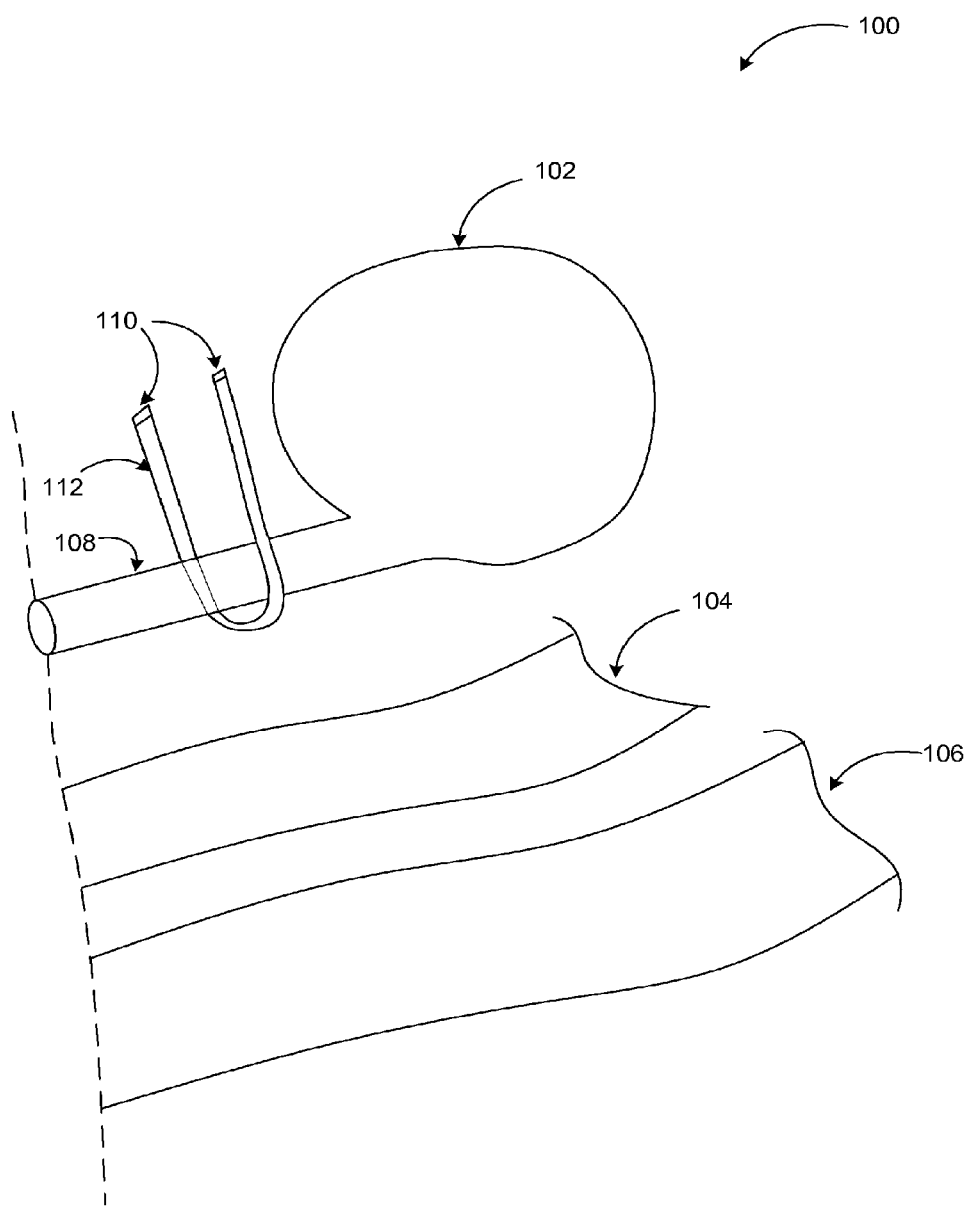
FIG. 1 illustrates an example anatomical layout of the pelvic cavity including the bladder, urethra, vagina, and colon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to providing a trans-vaginal delivery device for positioning a sub-urethral sling.

Briefly stated, technologies are generally provided for a trans-vaginal sling delivery device for deploying a sub-urethral sling to treat urinary incontinence. A delivery tool coupled with an interior of a delivery tube may be advanced through the vagina, and a pointed end of the delivery tube may puncture the vaginal wall. A sub-urethral sling may be attached to the delivery tube, and the sling may be longitudinally wrapped into a reduced delivery profile around the delivery tool within the delivery tube. The delivery tube may include a longitudinal slit opening, and the sling may be deployed from the delivery tool by rotating the delivery tool. Two delivery tubes and delivery tools may be employed to deploy each end of the sling, such that each end of the sling may be anchored on a right and left side of the urethra with a portion of the sling supporting the urethra from beneath.

FIG. 1 illustrates an example anatomical layout of the pelvic cavity including the bladder, urethra, vagina, and colon, arranged in accordance with at least some embodiments as described herein. As illustrated in diagram 100, the basic pelvic anatomy of a female includes a bladder 102, a vagina 104, and a colon 106. The bladder 102 stores urine, and a urethra 108 is a short narrow tube connected to the bladder 102 that carries the urine from the bladder 102 out of the body. Some females may experience incontinence, which may be the inability to control leakage of bladder. A common solution for helping treat incontinence is the use of a sub-urethral sling 112.

In some embodiments, an example sub-urethral sling 112 may be an elongated mesh ribbon or tape, a middle portion of which may be positioned underneath the urethra 108 for supporting the urethra 108 from beneath. Each end 110 of the sub-urethral sling 112 may be anchored in position above and to either side of the urethra in soft tissue surrounding the bladder for holding the sub-urethral sling 112 in place for supporting the urethra 108 from beneath. When the ends 110 are anchored in the soft tissue, the middle portion of the sub-urethral sling 112 that extends between the two ends 110 may be underneath the urethra 108, and may provide support by holding up the urethra 108.

In an example embodiment, the ends 110 of the sub-urethral sling 112 may be positioned slightly posterior in relation to the middle portion of the sub-urethral sling 112, such that the middle portion of the sub-urethral sling 112 is positioned an angle pointing towards the obturator foramen of the pelvic bone. In some example embodiments, the ends 110 of the sub-urethral sling 112 may be positioned through the obturator foramen. The obturator foramen is the hole created by the ischium and pubis bones of the pelvis through which nerves and muscles pass and is located posteriorly in relation to the urethra 108. The ends 110 may be passively or self-anchored in the soft tissue. For example, the ends 110 of the sub-urethral sling 112 may include barbs that enable the ends 110 to embed in the soft tissue naturally without requiring sutures. In other embodiments, the ends 110 may be anchored in place employing sutures or other similar anchoring techniques.

Figure 2:
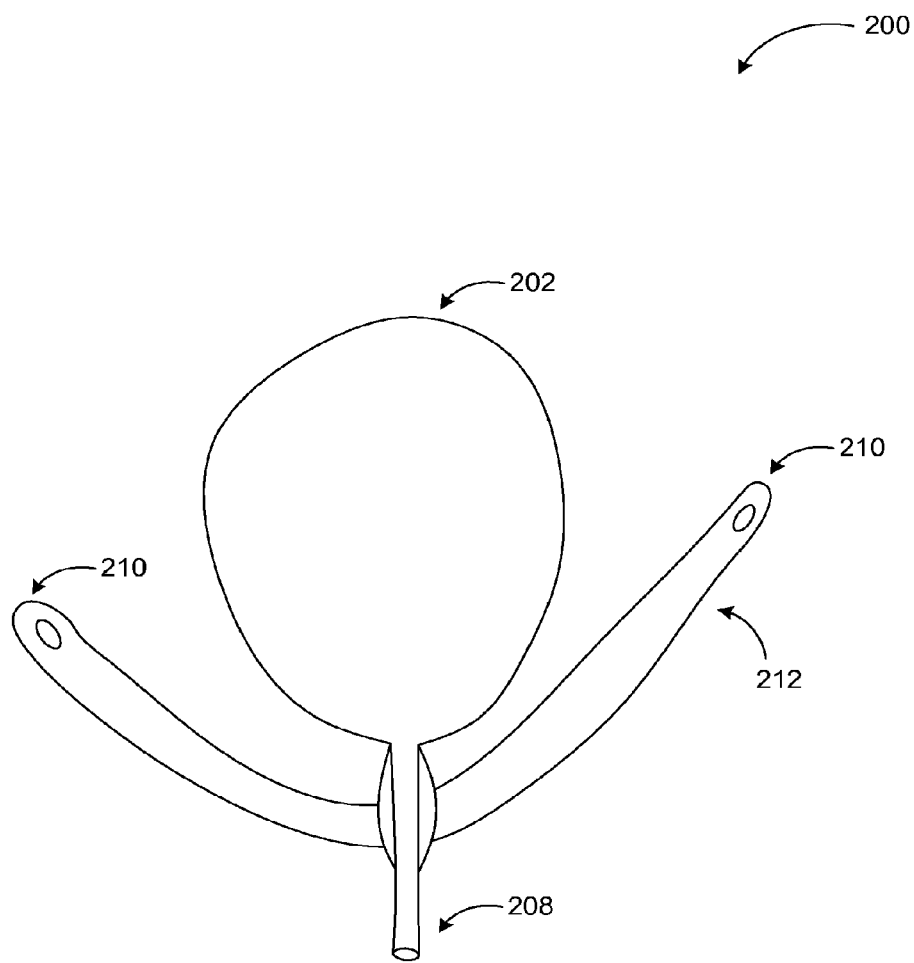
FIG. 2 illustrates an example urethral sling in position for supporting a urethra.

FIG. 2 illustrates an example urethral sling in position for supporting a urethra, arranged in accordance with at least some embodiments as described herein. As previously described, a sub-urethral sling 212 may be an elongated and substantially thin and flat mesh ribbon or tape. As illustrated in diagram 200, the sub-urethral sling 212 may deployed into an expanded position such that a middle portion of the sub-urethral sling 212 may be positioned underneath a urethra 208 for supporting the urethra 208 from beneath. Two ends 210 of the sub-urethral sling 122 may be positioned in the direction of and/or through the obturator foramen, such that the middle portion of the sub-urethral sling 212 is positioned an angle pointing towards the obturator foramen of the pelvic bone.

In a system according to embodiments, the sub-urethral sling 212 may be delivered and positioned employing minimally invasive surgery techniques in order to reduce risks, bleeding, recovery time, and pain for the patient. In order for the sub-urethral sling 212 to be inserted into the body and deployed to the expanded position, the sub-urethral sling 212 may be initially configured in a reduced delivery profile, or a more compact configuration, for enabling the sub-urethral sling 212 to be delivered through a minimally invasive technique. Once the sub-urethral sling 212 is delivered employing a minimally invasive technique as described herein, the sub-urethral sling 212 may be deployed into the expanded position such that the ends 210 may be anchored in a position in soft tissue surrounding the bladder 202 and urethra 208 for enabling the middle portion of the sub-urethral sling 212 to provide support to the urethra 208 from beneath.

Figure 3:
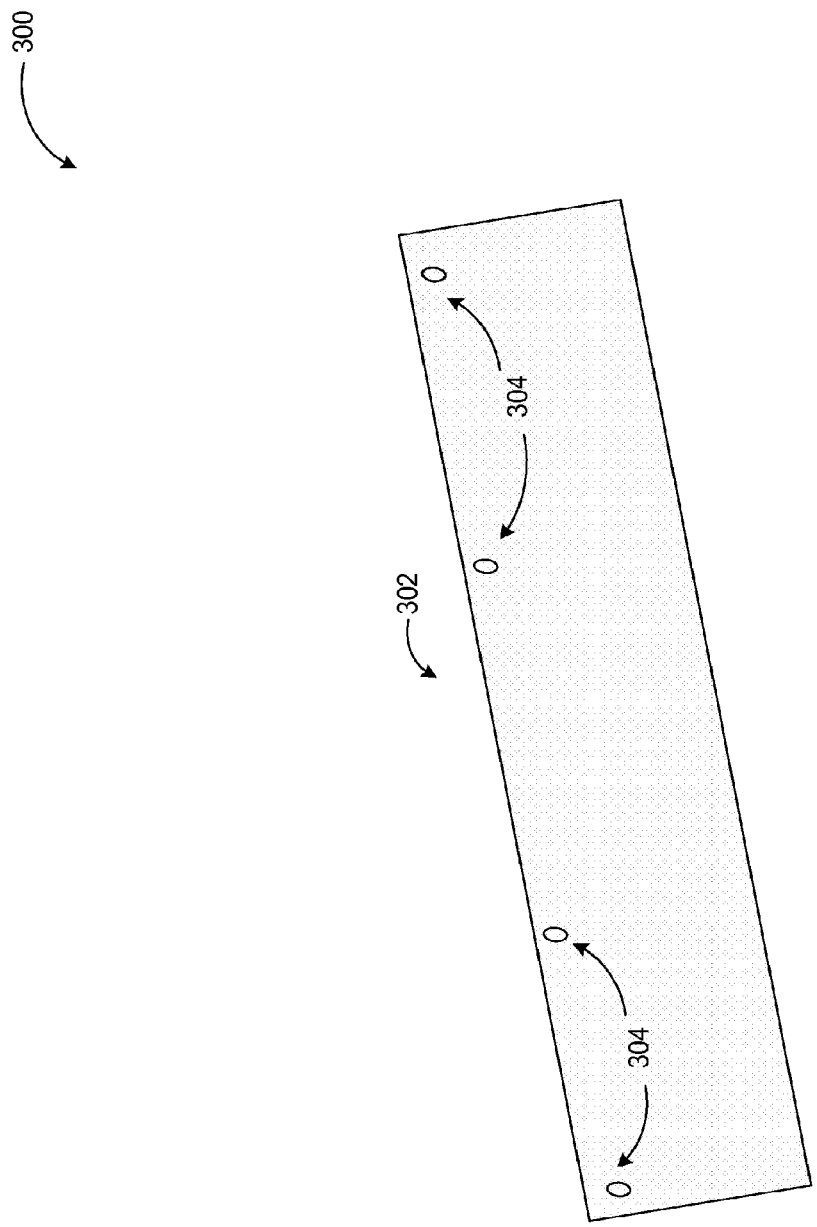
FIG. 3 illustrates a urethral sling with holes for attaching to a delivery tube.

FIG. 3 illustrates a urethral sling with holes for attaching to a delivery tube, arranged in accordance with at least some embodiments as described herein. As previously described, a sub-urethral sling 302 may be an elongated and substantially thin and flat mesh ribbon or tape. As illustrated in diagram 300, the sub-urethral sling 302 may include one or more holes 304 along one side of the sub-urethral sling 302. The holes 304 may enable the sub-urethral sling 302 to be attached to a delivery tool for wrapping the sub-urethral sling 302 in a reduced delivery profile for insertion through a delivery tube and deployment in a position to support a urethra. For example, the delivery tube may include one or more pins which may engage the holes 304 for attaching the sub-urethral sling 302 to the delivery tube.

Figure 4:
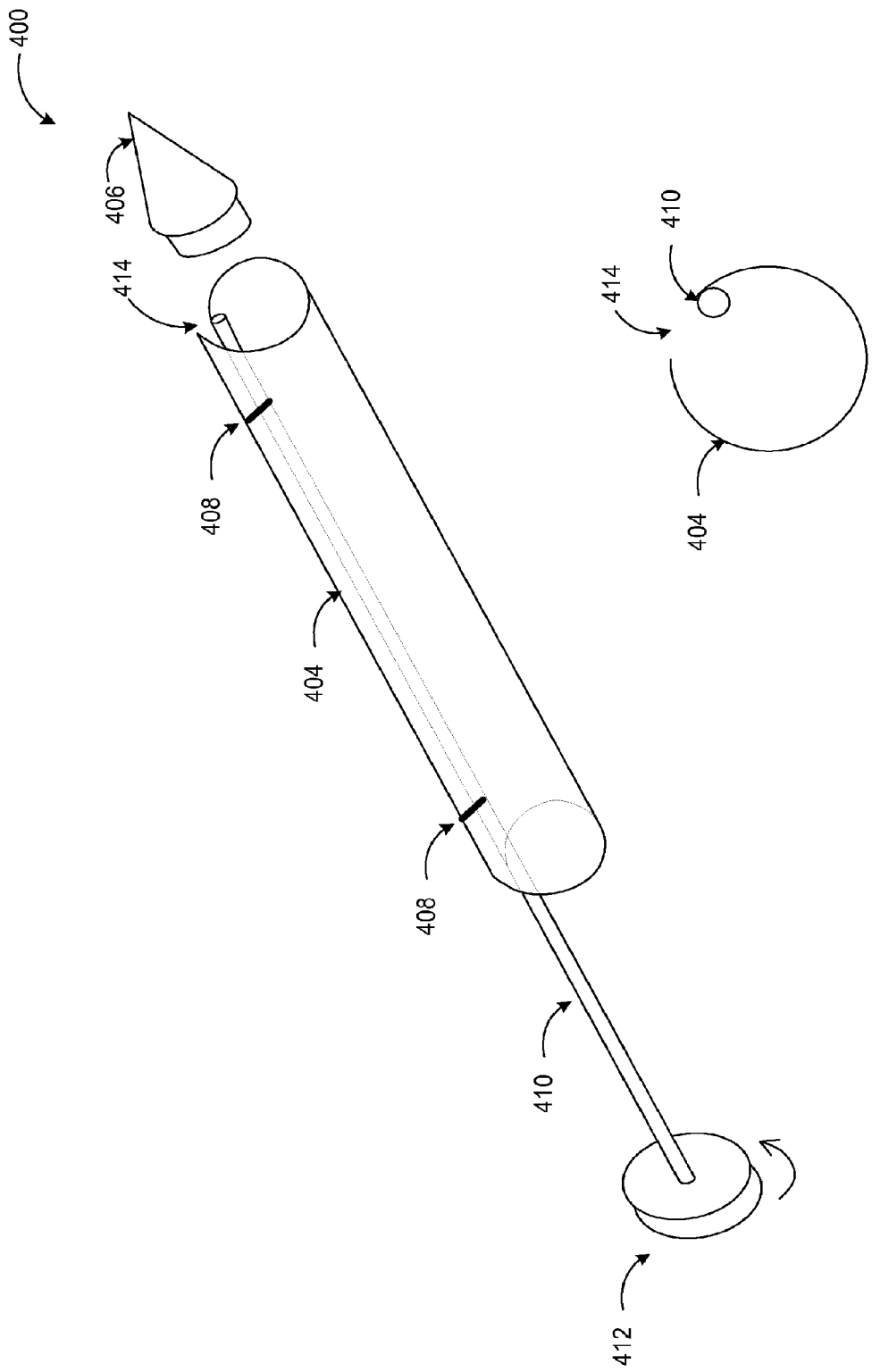
FIG. 4 illustrates an example delivery tube including an opening for deploying a urethral sling.

FIG. 4 illustrates an example delivery tube including an opening for deploying a urethral sling, arranged in accordance with at least some embodiments as described herein. As illustrated in diagram 400, a delivery tube 404 may be configured to deploy a sub-urethral sling in position to support a urethra. The delivery tube 404 may include a pointed distal end 406 for puncturing a hole in a vaginal wall. In an example embodiment, the delivery tube 404 may be advanced through the vagina, and the pointed distal end 406 may puncture a hole in an upper wall of the vagina. The delivery tube 404 may be advanced through the hole in the vaginal wall to provide access to the area surrounding the urethra near the bladder. The delivery tube 404 may also include one or more pins 408 along the length of the delivery tube 404 for enabling a sub-urethral sling to be attached to the delivery tube 404. As previously described, the sub-urethral sling may include one or more holes, and the pins 408 on the delivery tube 404 may engage the holes on the sub-urethral sling for enabling the sub-urethral sling to be temporarily attached to the delivery tube 404.

In an example embodiment, a delivery tool 410 may be coupled with the hollow interior of the delivery tube 404. The delivery tool 410 may be a long narrow rod configured to rotate within the hollow interior of the delivery tube 404 to deploy the sub-urethral sling out of the longitudinal slit opening 414. A handle portion 412 attached to a proximal end of the delivery tool 410 may remain outside the body and may enable the delivery tool 410 to be rotated by a physician. In an example scenario, the sub-urethral sling may be attached to the delivery tube 404, and the sub-urethral sling may be wrapped longitudinally around the delivery tool 410 within the delivery tube. The delivery tube 404 may include a longitudinal slit opening 414 along the length of the delivery tube 404 for enabling the sub-urethral sling to be deployed out of the longitudinal slit opening 414 by rotating the delivery tool 410. The delivery tube may be composed of a metal, such as stainless steel or nickel titanium alloy. Likewise the delivery tool may be composed of a metal, such as stainless steel or nickel titanium alloy.

Figure 5:
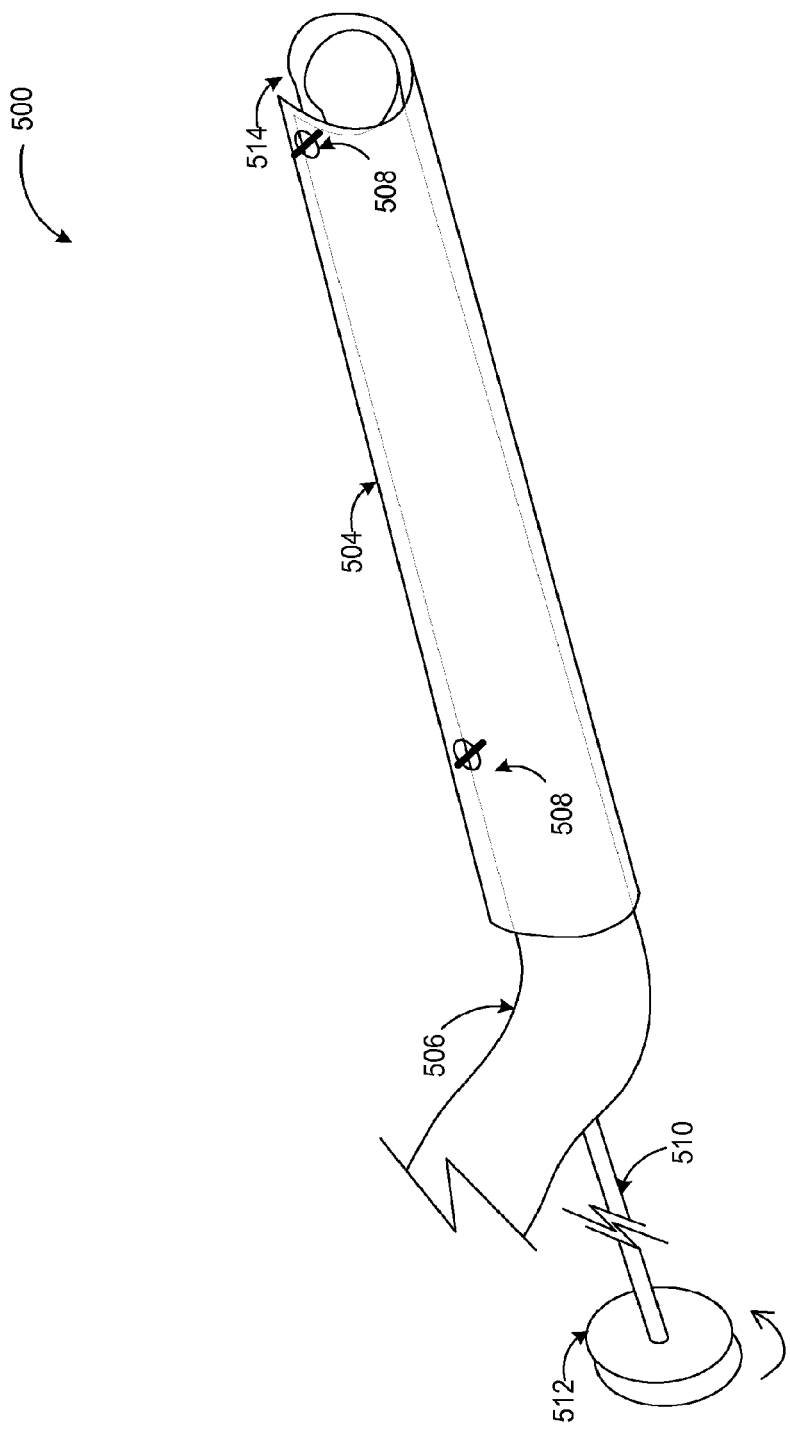
FIG. 5 illustrates a delivery tube and delivery tool with an attached urethral sling.

FIG. 5 illustrates a delivery tube and delivery tool with an attached urethral sling, arranged in accordance with at least some embodiments as described herein. In an example embodiment in a diagram 500, a sub-urethral sling 506 may be attached to the delivery tube 504 by engaging the holes of the sub-urethral sling 506 with one or more pins 508 included on the delivery tube 504. A delivery tool 510 may be coupled with the hollow interior of the delivery tube 504 and may be configured to rotate within the delivery tube 504 by rotating a handle 512 portion, which may remain outside of the body. The sub-urethral sling 506 may be wrapped into a reduced delivery profile along a longitudinal axis around the delivery tool 510 inside the delivery tube 504 by rotating the delivery tool 510. After the sub-urethral sling 506 is wrapped around the delivery tool 510 within the delivery tube, the sub-urethral sling 506 may be attached to the delivery tube 504 by engaging the pins 508 on the delivery tube with the holes on the edges of the sub-urethral sling 506. The delivery tube 504 may have a circular cross-sectional shape, and the inner diameter of the delivery tube 504 may be in a range configured to enable the delivery tool 510 and the attached sub-urethral sling 506 to be inserted within the interior of the delivery tube 504. For example an inner diameter may be in a range from about 4-6 mm. An example sub-urethral sling 506 may have a width in a range from about 1-2 cm, but some sub-urethral slings may have even wider widths, and they may be wrapped around the delivery tool 510 two or more times in order to fit within the delivery tube 504.

In an example embodiment, the delivery tube 504 including the attached sub-urethral sling 506, which may be longitudinally wrapped around the delivery tool 510 in the reduced delivery profile, may be advanced through the hole in the vaginal wall to the area surrounding the urethra near the bladder. The sub-urethral sling 506 may then be deployed out of the delivery tube 504. The sub-urethral sling 506 may be deployed out of the delivery tube 504 by initially rotating the delivery tool 510 to disengage the pins 508 from the holes in the sub-urethral sling 506 to release the sub-urethral sling 506 from the delivery tube 504. The delivery tool 510 may be further rotated, such that the sub-urethral sling 506 may deploy out of a longitudinal slit opening 514 along the length of the delivery tube. The delivery tool 510 may facilitate anchoring each end of the sub-urethral sling 506 in a position to each of the right side and the left side of the urethra, with a middle portion that extends between each end of the sub-urethral sling 506 positioned underneath the urethra to provide support from beneath. Once in position, the delivery tube 504 may be removed from the vagina.

Figure 6:
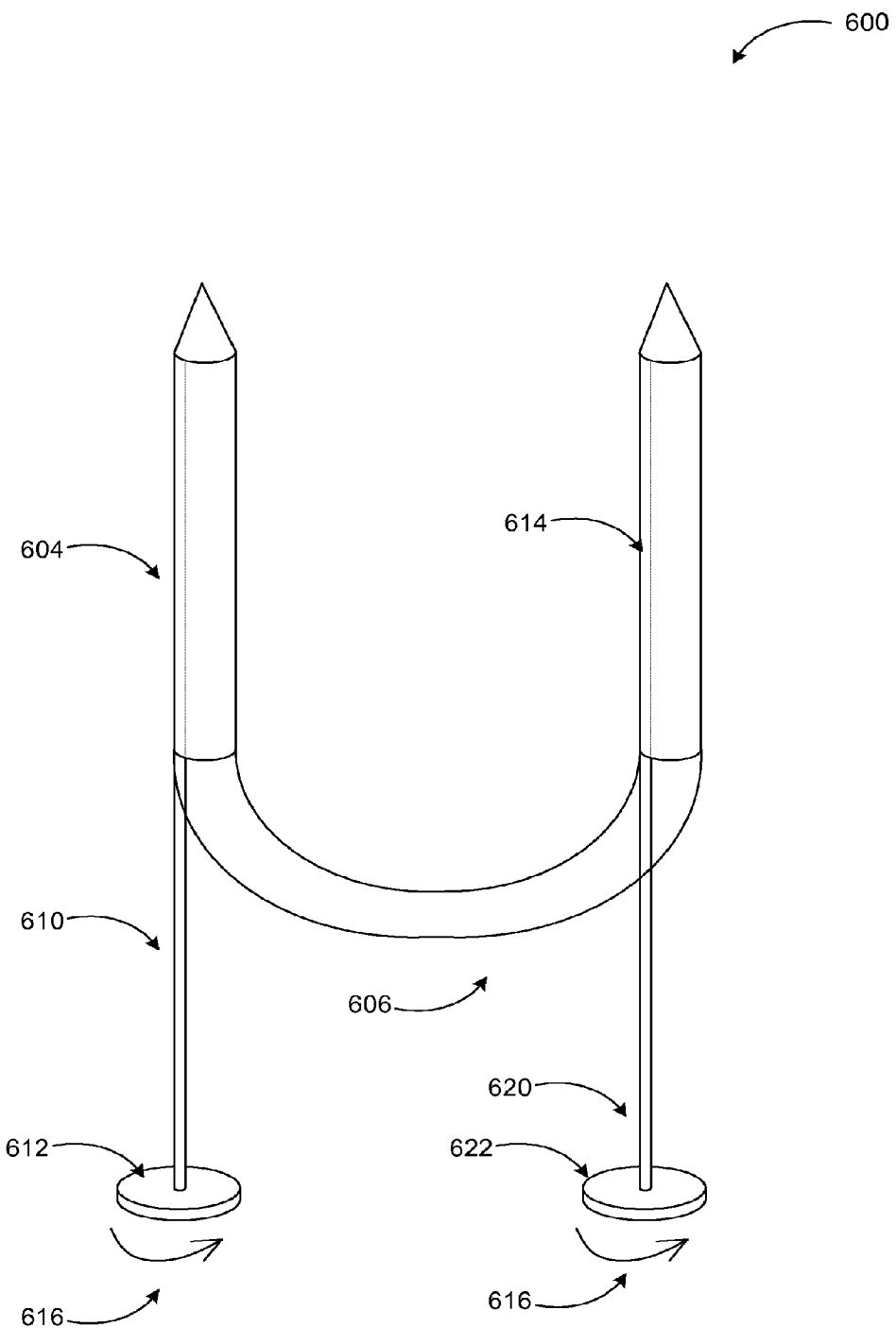
FIG. 6 illustrates an example configuration of a first and second delivery tube for attaching a urethral sling.

FIG. 6 illustrates an example configuration of a first and second delivery tube for attaching a urethral sling, arranged in accordance with at least some embodiments as described herein. As illustrated in diagram 600, two delivery tubes may be employed for deploying and positioning a sub-urethral sling 606 in a position to support a urethra. A first delivery tube 604 may include a longitudinal opening along the length of the first delivery tube 604, and a first delivery tool 610 may be coupled with the hollow interior of the first delivery tube 604. The first delivery tool 610 may include a handle 612 which may remain outside the body to enable the first delivery tool 610 to be rotated 616 by turning the handle 612. Likewise, a second delivery tube 614 may include a longitudinal opening along the length of the second delivery tube 614, and a second delivery tool 620 may be coupled with the hollow interior of the second delivery tube 614. The second delivery tool 620 may also include a handle 622 which may remain outside the body to enable the second delivery tool 620 to be rotated by turning the handle 622.

In an example embodiment, a first end of the sub-urethral sling 606 may be attached to the first delivery tube 604, and the first end of the sub-urethral sling 606 may be longitudinally wrapped around the first delivery tool 610 within the first delivery tube 604. The first end of the sub-urethral sling 606 may be attached to the first delivery tube 604 by engaging pins included on the first delivery tube 604 with one or more holes on the first end of the sub-urethral sling 606. Similarly, a second end of the sub-urethral sling 606 may be attached to the second delivery tube 614, and the second end of the sub-urethral sling 606 may be longitudinally wrapped around the second delivery tool 620 within the second delivery tube 614. The second end of the sub-urethral sling 606 may be attached to the second delivery tube 614 by engaging pins included on the second delivery tube 614 with one or more holes on the second end of the sub-urethral sling 606. When both ends of the sub-urethral sling 606 are attached to the first and second delivery tubes 604, 614, a middle portion of the sub-urethral sling 606 that extends between the first end and the second end may remain outside of each of the first and second delivery tubes 604, 614.

Figure 7:
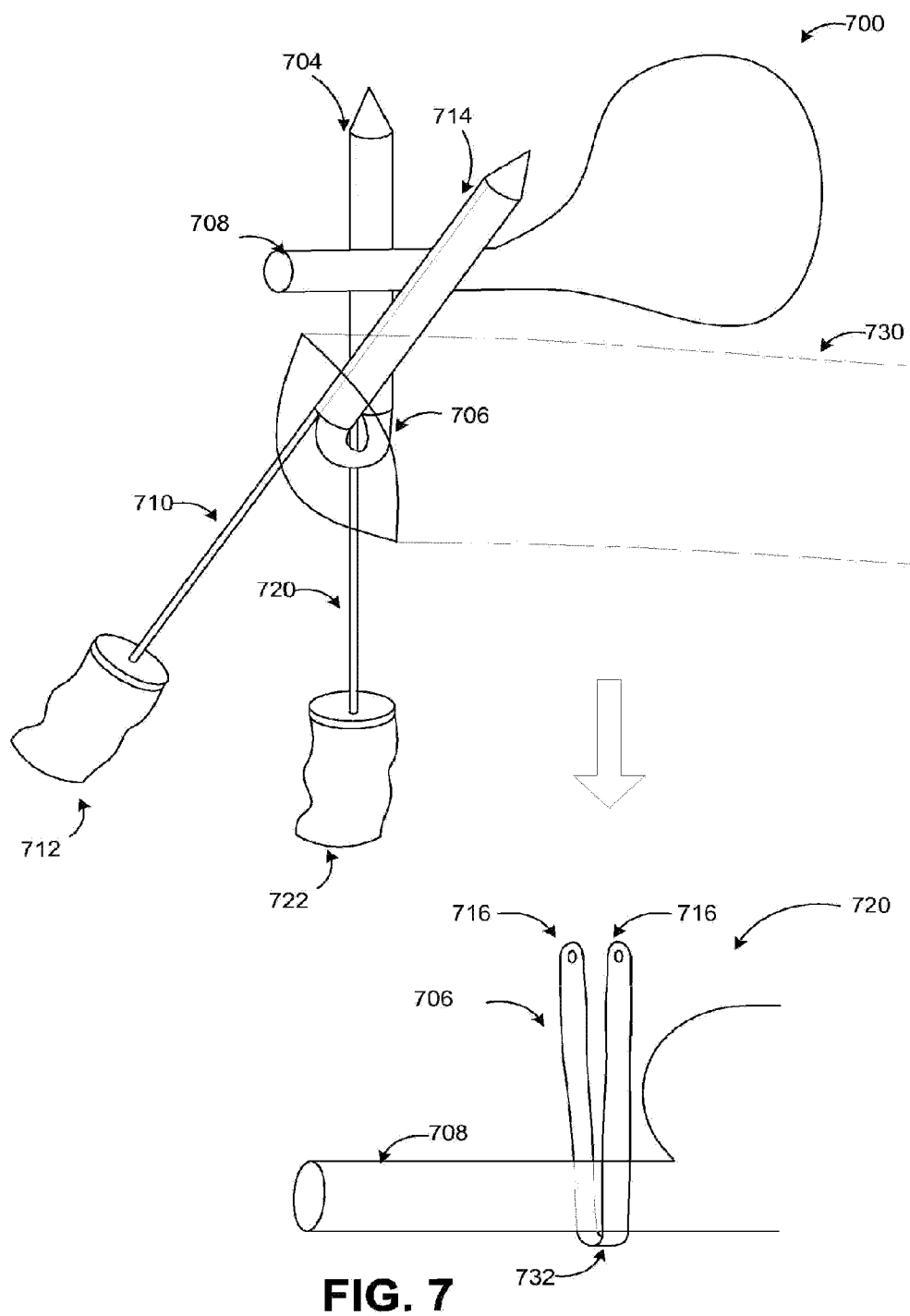
FIG. 7 illustrates an example configuration of a trans-vaginal delivery device in position for delivering a urethral sling, all arranged in accordance with at least some embodiments as described herein.

FIG. 7 illustrates an example configuration of a trans-vaginal delivery device in position for delivering a urethral sling, arranged in accordance with at least some embodiments as described herein. In an example configuration 700, a first end of a sub-urethral sling 706 may be attached to a first delivery tube 704 and wrapped around a first delivery tool 710 coupled with the interior of the first delivery tube 704. A second end of the sub-urethral sling 706 may be attached to a second delivery tube 714 and wrapped around a second delivery tool 720 coupled with the interior of the second delivery tube 714. The first delivery tube 704 and the second delivery tube 714 may be inserted into the vagina 730, and a pointed distal end of one of the first and second delivery tubes may puncture the upper interior wall of the vagina 730. The first delivery tube 704 and the second delivery tube 714 may be advanced through the puncture in the upper vaginal wall to provide access to the area surrounding a urethra 708 near the bladder.

In an example embodiment, the first delivery tool 710 may be rotated by rotating a handle 712 on a proximal end of the first delivery tool 710 to disengage the pins from the holes in the first end of the sub-urethral sling 706, and deploy the first end of the sub-urethral sling 706 out of a longitudinal slit opening along the first delivery tube 704. Similarly, the second delivery tool 720 may be rotated by rotating a handle 722 on a proximal end of the second delivery tool 720 to disengage the pins from the holes in the second end of the sub-urethral sling 706 to release the second end of the sub-urethral sling 706 from the second delivery tube 714, and to deploy the second end of the sub-urethral sling 706 out of a longitudinal slit opening along the second delivery tube 714. When the first end and the second end of the sub-urethral sling 706 have been deployed out of each of the first delivery tube 704 and the second delivery tube 714, first end and the second end may be released from the first delivery tube 704 and the second delivery tube 714.

In an example embodiment, as illustrated in diagram 720, once each end 716 of the sub-urethral sling 706 have been released from the first and second delivery tubes 704, 714, the first and second delivery tools 710, 720 may facilitate anchoring each end 716 of the sub-urethral sling 706 in a position to support the urethra 708. For example, the first end of the sub-urethral sling 706 may be anchored to one of the right side and the left side of the urethra 708, and the second end of the 706 may be anchored to the other of the right side and the left side of the urethra 708. The middle portion 732 that extends between each end 716 of the sub-urethral sling 506 may remain slack between the first delivery tube and the second delivery tube while the first and second ends of the 706 are being positioned. Once the first and second ends of the sub-urethral sling 706 are anchored in position, the first delivery tool 710 and the second delivery tool 720 may apply tension to position the middle portion 732 underneath the urethra 708 to provide support from beneath. Once the 706 is in the desired position for supporting the urethra 708, the first delivery tube 704 and the second delivery tube 714 may be removed from the vagina.

In another example embodiment, a single delivery tube may be employed to anchor both ends of the sub-urethral sling 706 in position for supporting the urethra. The first end of the sub-urethral sling 706 may be attached to the delivery tube and wrapped in a reduced delivery profile around a delivery tool coupled with the first delivery tube. The delivery tube may advance through the vagina and deploy the first end of the sub-urethral sling in position on one of the right side and the left side of the urethra. After anchoring the first end, the delivery tube may be removed, and the second end of the sub-urethral sling 706 may be attached to the delivery tube and wrapped around the delivery tool coupled with the first delivery tube. The delivery tube may advance through the vagina and deploy the second end of the sub-urethral sling in position on the other of the right side and the left side of the urethra.

While embodiments have been discussed above using specific examples, components, and configurations, they are intended to provide a general guideline to be used for—providing a trans-vaginal sling delivery device for deploying a sub-urethral sling to treat urinary incontinence. These examples do not constitute a limitation on the embodiments, which may be implemented using other components, modules, and configurations using the principles described herein. Furthermore, actions discussed above may be performed in various orders, especially in an interlaced fashion.

According to some example embodiments, the present disclosure describes a trans-vaginal delivery device for positioning a sub-urethral sling. The trans-vaginal delivery device may include a delivery tube having a substantially pointed distal end for puncturing a wall of a vagina and having a longitudinal slit opening along the delivery tube, a sub-urethral sling configured to be wrapped into a reduced delivery profile for delivery through the delivery tube, and a delivery tool coupled with an interior portion of delivery tube, the delivery tool configured to deploy the sub-urethral sling in a position for supporting the urethra.

According to some examples, the delivery tube may be configured to advance through the vagina and puncture through an upper wall of the vagina. The delivery tube may have a substantially circular cross sectional shape with a diameter in a range configured to enable the delivery tool and the sub-urethral sling in the reduced delivery profile within a hollow interior of the delivery tube. The delivery tube may be configured to pass through the punctured wall of the vagina into an interior space near the urethra. The delivery tube includes two or more pins for enabling the sub-urethral sling to be attached to the delivery tube.

According to some examples, the sub-urethral sling includes two or more holes for enabling the sub-urethral sling to be attached to the delivery tube by engaging the two or more pins through the two or more holes. The sub-urethral sling may be wrapped into the reduced delivery profile around the delivery tool along a longitudinal axis of the sub-urethral sling. The sub-urethral sling may be configured to be deployed into position at the urethra by unwrapping the sub-urethral sling from the delivery tool and deploying the urethral sling out of the delivery tube through the longitudinal slit opening. The delivery tool includes a handle portion on a proximal end of the delivery tool for enabling the delivery tool to be rotated for unwrapping the sub-urethral sling from the delivery tool and deploying the sub-urethral sling out of the delivery tube through the longitudinal slit opening.

According to some examples, the sub-urethral sling from the delivery tube may be configured to be released from the delivery tube by disengaging the two or more pins from the two or more holes. A first end of the sub-urethral sling may be anchored in soft tissue on a left side of the urethra, a middle portion that extends between the first end and a second end of the sub-urethral sling may be positioned underneath the urethra, and the second end of the sub-urethral sling may be anchored in soft tissue on a right side of the urethra, such that the sub-urethral sling supports the urethra from beneath. The delivery tube may be composed of a metal. The metal may be one of stainless steel or nickel titanium alloy. The delivery tool may be composed of one of stainless steel or nickel titanium alloy.

According to some examples, the present disclosure describes a trans-vaginal delivery device for positioning a sub-urethral sling. The trans-vaginal delivery device may include a first delivery tube having a substantially pointed distal end and having a longitudinal slit opening along the first delivery tub, the first delivery tube configured to advance through the vagina and puncture through an upper wall of the vagina, a first delivery tool coupled with the first delivery tube, the first delivery tool configured to deploy a first end of the sub-urethral sling out of the first delivery tube through the longitudinal slit opening, a second delivery tube having a substantially pointed distal end and having a longitudinal slit opening along the second delivery tube, and a second delivery tool coupled with an interior of the second delivery tube, the second delivery tube and the second delivery tool configured to pass through the puncture in the upper wall of the vagina, wherein the second delivery tool may be configured to deploy a second end of the sub-urethral sling out of the second delivery tube through the longitudinal slit opening.

According to some examples, the first delivery tube coupled with the first delivery tool and the second delivery tube coupled with the second delivery tool may be configured to pass through the puncture in the upper wall of the vagina into an interior space near the urethra. The second delivery tube may be configured to advance through the vagina and puncture a second hole in an upper wall of the vagina, and the second delivery tube coupled with the second delivery tool may be configured to pass through the second hole in the upper wall of the vagina into an interior space near the urethra.

According to other examples, the present disclosure describes a method for delivering a sub-urethral sling employing a trans-vaginal delivery device. The method may include advancing a delivery tube having a longitudinal slit opening along the delivery tube and having a substantially pointed distal end through a vagina such that an upper interior wall of the vagina may be punctured, coupling a delivery tool with an interior portion of the delivery tube, attaching a first end of a sub-urethral sling to the delivery tube, wrapping a sub-urethral sling in a reduced delivery profile around the delivery tool, passing the delivery tube including the delivery tool and attached sub-urethral sling through the punctured upper interior wall of the vagina, and deploying the sub-urethral sling in a position for supporting the urethra.

According to some examples, the method may include attaching the first end of the sub-urethral sling to the delivery tube by engaging two or more holes included in the sub-urethral sling with two or more pins included on the delivery tube. The method may also include wrapping the sub-urethral sling along a longitudinal axis of the delivery tool such that the sub-urethral sling may be configured in the reduced delivery profile around the delivery tool. The method may also include attaching a handle portion on a proximal end of the delivery tool for enabling the delivery tool to be rotated to deploy the sub-urethral sling out of the delivery tube through the longitudinal slit opening.

According to some examples, the method may also include deploying the sub-urethral sling for supporting the urethra by rotating the delivery tool to unwrap the sub-urethral sling from the delivery tool and guide the sub-urethral sling out of the delivery tube through the longitudinal slit opening, releasing the sub-urethral sling from the delivery tool, and anchoring a first end of the sub-urethral sling on one of a left side or a right side of the urethra, positioning a middle portion that extends between the first end and a second end of the sub-urethral sling underneath the urethra, and anchoring the second end of the sub-urethral sling on the other of the left side and the right side of the urethra employing the delivery tool. The method may also include disengaging the two or more pins from the two or more holes for releasing the sub-urethral sling from the delivery tool. The method may also include anchoring a first end of the sub-urethral sling in soft tissue in a position above and on one of the right side and the left side of the urethra employing the delivery tool, swiveling the delivery tube such that the distal end of the delivery tube extends towards the other of the right side and the left side of the urethra, and anchoring the second end of the sub-urethral sling in a position above and on the other of the right side and the left side of the urethra employing the delivery tool.

According to other examples, the present disclosure describes a method for delivering a sub-urethral sling employing a trans-vaginal delivery device. The method may include employing a first delivery tube having a substantially pointed distal end and having a longitudinal opening along the first delivery tube for enabling a first delivery tool to deploy and position a first end of the sub-urethral sling in a position above and on one of the right side and the left side of the urethra, and employing a second delivery tube having a longitudinal opening along the second delivery tube for enabling a second delivery tool to deploy and position a second end of the sub-urethral sling in a position above and on the other of the right side and the left side of the urethra.

According to other examples, the method may include passing the first delivery tube including the first delivery tool and attached first end of the sub-urethral sling through the punctured upper interior wall of the vagina, passing the second delivery tube including the second delivery tool and attached second end of the sub-urethral sling through the punctured upper interior wall of the vagina, rotating the first delivery tool to deploy the first end of the sub-urethral sling from the longitudinal opening in the first delivery tube, releasing the first end of the sub-urethral sling from the first delivery tube rotating the second delivery tool to deploy the second end of the sub-urethral sling from the longitudinal opening in the second delivery tube, releasing the second end of the sub-urethral sling from the second delivery tube, anchoring the first end of the sub-urethral sling on one of the right side and the left side of the urethra, anchoring the second end of the sub-urethral sling on the other of the left side of the urethra, and applying tension employing the first delivery tool and the second delivery tool for positioning a middle portion that extends between the first end and the second end of the sub-urethral sling underneath the urethra such that the sling in the position for supporting the urethra.

According to other examples, the present disclosure describes a system for delivering a sub-urethral sling employing a trans-vaginal delivery device. The system may include a delivery tube having a substantially pointed distal end for puncturing a wall of a vagina and having a longitudinal slit opening along the delivery tube, a sub-urethral sling configured to be wrapped into a reduced delivery profile for delivery through the delivery tube, and a delivery tool coupled with an interior portion of delivery tube, the delivery tool configured to deploy the sub-urethral sling in a position for supporting the urethra.

According to some examples, the delivery tube may be configured to advance through the vagina and puncture through an upper wall of the vagina into an interior space near the urethra. The delivery tube includes two or more pins for enabling the sub-urethral sling to be attached to the delivery tube. The sub-urethral sling includes two or more holes for enabling the sub-urethral sling to be attached to the delivery tool by engaging the two or more pins through the two or more holes. The sub-urethral sling may be wrapped into the reduced delivery profile around the delivery tool along a longitudinal axis of the sub-urethral sling.

According to some examples, the sub-urethral sling may be configured to be deployed into position by unwrapping the sub-urethral sling from the delivery tool and deploying the urethral sling out of the delivery tube through the longitudinal slit opening. The delivery tool includes a handle portion on a proximal end for enabling the delivery tool to be rotated for deploying the urethral sling out of the delivery tube through the longitudinal slit opening. The sub-urethral sling from the delivery tube may be configured to be released from the delivery tube by disengaging the two or more pins from the two or more holes.

According to some examples, a first end of the sub-urethral sling may be anchored in soft tissue on a left side of the urethra, a middle portion that extends between the first end and a second end of the sub-urethral sling may be positioned underneath the urethra, and the second end of the sub-urethral sling may be anchored in soft tissue on a right side of the urethra, such that the sub-urethral sling supports the urethra from beneath.

According to further examples, the present disclosure also describes a method of manufacturing a trans-vaginal delivery device for delivery of a sub-urethral sling. The method may include forming a delivery tube having a substantially pointed distal end for puncturing a wall of a vagina and having an opening longitudinally along the delivery tube, configuring a sub-urethral sling to be wrapped into a reduced delivery profile for delivery through the delivery tube, and coupling a delivery tool with an interior portion of the delivery tube, the delivery tool configured to advance the sub-urethral sling through the delivery tube to deploy the sub-urethral sling in a position for supporting the urethra. The method may include configuring the delivery tube to have a substantially circular cross sectional shape with a diameter in a range configured to enable the delivery tool and the sub-urethral sling in the reduced delivery profile to fit within a hollow interior of the delivery tube.

According to some example, the method may include attaching two or more pins to the delivery tube for enabling the sub-urethral sling to be attached to the delivery tube. The method may include forming two or more holes in the sub-urethral sling for enabling the sub-urethral sling to be attached to the delivery tool by engaging the two or more pins through the two or more holes. The method may include attaching a handle portion on a proximal end of the delivery tool for enabling the delivery tool to be rotated for deploying the urethral sling out of the delivery tube through the longitudinal slit opening. The method may include composing the delivery tube from a metal. The method may include composing the delivery tube from one of stainless steel or nickel titanium alloy. The method may include composing the delivery tool from one of stainless steel or nickel titanium alloy.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A trans-vaginal delivery device to position a sub-urethral sling, the trans-vaginal delivery device comprising:
    a delivery tube that includes:
        a substantially pointed distal end that punctures a wall of a vagina,
        a longitudinal slit opening along the delivery tube, and
        two or more pins to enable the sub-urethral sling to be attached to the delivery tube;
    the sub-urethral sling that includes:
        two or more holes to enable the sub-urethral sling to be attached to the delivery tube, wherein the two or more holes are configured to be wrapped into a reduced delivery profile around a delivery tool two or more times for delivery through the delivery tube; and
    the delivery tool coupled with an interior portion of delivery tube, wherein the delivery tool is configured to:
        deploy the sub-urethral sling to support a urethra;
        anchor a first end of the sub-urethral sling to a position to a left side of the urethra;
        anchor a second end of the sub-urethral sling in another position to a right side of the urethra; and
        extend a middle portion of the sub-urethral sling between the anchored first end and the anchored second end at an angle towards an obturator foramen of a pelvic bone.

2. The trans-vaginal delivery device of claim 1, wherein the delivery tube is configured to advance through the vagina and puncture through an upper wall of the vagina.

3. The trans-vaginal delivery device of claim 2, wherein the delivery tube has a substantially circular cross-sectional shape with a diameter in a range configured to enable the delivery tool and the sub-urethral sling in the reduced delivery profile within a hollow interior of the delivery tube.

4. The trans-vaginal delivery device of claim 2, wherein the delivery tube is configured to pass through the punctured wall of the vagina into an interior space near the urethra.

5. The trans-vaginal delivery device of claim 1, wherein the sub-urethral sling includes two or more holes to enable the sub-urethral sling to be attached to the delivery tube to engage the two or more pins through the two or more holes.

6. The trans-vaginal delivery device of claim 1, wherein the sub-urethral sling is wrapped into the reduced delivery profile around the delivery tool along a longitudinal axis of the sub-urethral sling.

7. The trans-vaginal delivery device of claim 6, wherein the sub-urethral sling is deployed into the urethra by:
    unwrapping the sub-urethral sling from the delivery tool; and
    deploying the urethral sling out of the delivery tube through the longitudinal slit opening.

8. The trans-vaginal delivery device of claim 7, wherein the delivery tool includes a handle portion on a proximal end of the delivery tool to enable the delivery tool to be rotated to unwrap the sub-urethral sling from the delivery tool and to deploy the sub-urethral sling out of the delivery tube through the longitudinal slit opening.

9. The tran-vaginal delivery device of claim 8, wherein the sub-urethral sling from the delivery tube is configured to be released from the delivery tube to disengage the two or more pins from the two or more holes.

10. The trans-vaginal delivery device of claim 1, wherein the first end of the sub-urethral sling is anchored in a soft tissue on the left side of the urethra, the middle portion that extends between the first end and the second end of the sub-urethral sling is positioned underneath the urethra, and the second end of the sub-urethral sling is anchored in the soft tissue on the right side of the urethra, such that the sub-urethral sling supports the urethra from beneath.

11. The trans-vaginal delivery device of claim 1, wherein the delivery tube is composed of a metal.

12. The trans-vaginal delivery device of claim 11, wherein the metal includes one of stainless steel and nickel titanium alloy.

13. The trans-vaginal delivery device of claim 1, wherein the delivery tool includes one of stainless steel and nickel titanium alloy.

14. A trans-vaginal delivery device to position a sub-urethral sling, the trans-vaginal delivery device comprising:
    a first delivery tube that includes:
        a substantially pointed distal end,
        a longitudinal slit opening along the first delivery tube, and
        two or more pins to enable the sub-urethral sling to be attached to the first delivery tube, wherein the first delivery tube is configured to advance through a vagina and puncture through an upper wall of the vagina;

a first delivery tool coupled with the first delivery tube, wherein the first delivery tool is configured to:
deploy a first end of the sub-urethral sling out of the first delivery tube through the longitudinal slit opening, wherein the sub-urethral sling is wrapped into a reduced delivery profile around the first delivery tool two or more times along a longitudinal axis of the sub-urethral sling; and
anchor the first end of the sub-urethral sling to a position to a left side of a urethra;

a second delivery tube that includes:
a substantially pointed distal end,
a longitudinal slit opening along the second delivery tube, and
two or more pins to enable the sub-urethral sling to be attached to the second delivery tube; and a second delivery tool coupled with an interior of the second delivery tube, wherein the second delivery tube and the second delivery tool are configured to pass through the puncture in the upper wall of the vagina, and wherein the second delivery tool is configured to:
deploy a second end of the sub-urethral sling out of the second delivery tube through the longitudinal slit opening, wherein the sub-urethral sling is wrapped into a reduced delivery profile around the second delivery tool two or more times along a longitudinal axis of the sub-urethral sling;
anchor the second end of the sub-urethral sling in another position to a right side of the urethra, and
extend a middle portion of the sub-urethral sling between the anchored first end and the anchored second end at an angle towards an obturator foramen of a pelvic bone.

15. The trans-vaginal delivery device of claim 14, wherein the first delivery tube is coupled with the first delivery tool and the second delivery tube is coupled with the second delivery tool, and wherein the first delivery tool and the second delivery tool are configured to pass through the puncture in the upper wall of the vagina into an interior space near the urethra.

16. The trans-vaginal delivery device of claim 14, wherein the second delivery tube is configured to advance through the vagina and puncture a second hole in the upper wall of the vagina, and wherein the second delivery tube coupled with the second delivery tool are configured to pass through the second hole in the upper wall of the vagina into an interior space near the urethra.

17. A method to deliver a sub-urethral sling that employs a trans-vaginal delivery device, the method comprising:
advancing a delivery tube that includes:
a longitudinal slit opening along the delivery tube,
a substantially pointed distal end, and
two or more pins to enable the sub-urethral sling to be attached to the delivery tube through a vagina such that an upper interior wall of the vagina is punctured;
coupling a delivery tool with an interior portion of the delivery tube;
attaching a first end of the sub-urethral sling to the delivery tube, wherein the sub-urethral sling includes two or more holes to enable the sub-urethral sling to be attached to the delivery tube;
wrapping the sub-urethral sling in a reduced delivery profile around the delivery tool two or more times along a longitudinal axis of the sub-urethral sling;
passing the delivery tube that includes the delivery tool and the attached sub-urethral sling through a punctured upper interior wall of the vagina;
deploying the sub-urethral sling to support a urethra;
anchoring the first end of the sub-urethral sling to a position to a left side of the urethra;
anchoring a second end of the sub-urethral sling in another position to a right side of the urethra; and
extending a middle portion of the sub-urethral sling between the anchored first end and the anchored second end at an angle towards an obturator foramen of a pelvic bone.

18. The method of claim 17, further comprising:
attaching the first end of the sub-urethral sling to the delivery tube to engage two or more holes included in the sub-urethral sling with two or more pins included on the delivery tube.

19. The method of claim 17, further comprising:
attaching a handle portion on a proximal end of the delivery tool to:
enable the delivery tool to be rotated to unwrap the sub-urethral sling from the delivery tool; and
deploy the sub-urethral sling out of the delivery tube through the longitudinal slit opening.

20. The method of claim 19, wherein deploying the sub-urethral sling to support the urethra includes:
rotating the delivery tool to unwrap the sub-urethral sling from the delivery tool; and
guiding the sub-urethral sling out of the delivery tube through the longitudinal slit opening.

21. The method of claim 20, further comprising:
disengaging the two or more pins from the two or more holes to release the sub-urethral sling from the delivery tool.

22. The method of claim 21, further comprising:
anchoring the first end of the sub-urethral sling in a soft tissue in the position above and on the right side of the urethra that employs the delivery tool;
swiveling the delivery tube such that the distal end of the delivery tube extends towards the left side of the urethra; and
anchoring the second end of the sub-urethral sling in the other position above and on the left side of the urethra that employs the delivery tool.

23. The method of claim 22, further comprising:
applying tension that employs a first delivery tool and a second delivery tool to position a middle portion that extends between the first end and the second end of the sub-urethral sling underneath the urethra such that the sling supports the urethra.

* * * * *

UNITED STATES PATENT AND TRADEMARK OFFICE
CERTIFICATE OF CORRECTION

PATENT NO.       : 9,241,780 B2
APPLICATION NO.  : 14/112036
DATED            : January 26, 2016
INVENTOR(S)      : Adams et al.

It is certified that error appears in the above-identified patent and that said Letters Patent is hereby corrected as shown below:

Specification

In Column 1, below Title, Line 1, insert -- CROSS-REFERENCE TO RELATED APPLICATION --.

In Column 1, Line 4, delete "§371" and insert -- § 371 --, therefor.

Claims

In Column 14, Line 37, in Claim 9, delete "tran-vaginal" and insert -- trans-vaginal --, therefor.

Signed and Sealed this
Twenty-sixth Day of April, 2016

Michelle K. Lee
*Director of the United States Patent and Trademark Office*